United States Patent [19]

Haruta et al.

[11] Patent Number: 4,975,375

[45] Date of Patent: Dec. 4, 1990

[54] BIOCATALYST IMMOBILIZATION WITH A REVERSIBLY SWELLING AND SHRINKING POLYMER

[75] Inventors: Masahiro Haruta, Tokyo; Hirohide Munakata; Satoshi Yuasa, both of Yokohama; Yoko Yoshinaga, Machida; Yukuo Nishimura, Sagamihara, all of Japan

[73] Assignee: Canon Kabushiki Kaisha, Tokyo, Japan

[21] Appl. No.: 403,983

[22] Filed: Sep. 5, 1989

Related U.S. Application Data

[63] Continuation of Ser. No. 309,033, Feb. 2, 1989, abandoned, which is a continuation of Ser. No. 880,320, Jun. 30, 1986, abandoned.

[30] Foreign Application Priority Data

Jul. 2, 1985 [JP] Japan ................................ 60-144002
Aug. 12, 1985 [JP] Japan ................................ 60-175774

[51] Int. Cl.$^5$ ...................... C12N 11/04; C12N 11/02; G01N 33/545; G01N 33/544
[52] U.S. Cl. ................................... 435/482; 435/177; 436/528; 436/531; 530/812; 530/817
[58] Field of Search ............... 435/174, 177, 180, 182; 436/52.8, 531; 530/812, 817

[56] References Cited

U.S. PATENT DOCUMENTS

| | | | |
|---|---|---|---|
| 3,421,892 | 1/1969 | Taylor | 430/215 |
| 3,421,893 | 1/1969 | Taylor | 430/215 |
| 3,705,084 | 12/1972 | Reynolds | 435/180 |
| 4,070,348 | 1/1978 | Kraemer et al. | 435/180 X |
| 4,364,385 | 12/1982 | Lossef | 435/182 X |

OTHER PUBLICATIONS

Dahlqvist et al., "Hydrolysis of B-Galactosides Using Polymer-Entrapped Lactase-Free Milk", *Biotechnology and Bioengineering XV,* pp. 395–402 (1973).
Mosbach, "Matrix-Bound Enzymes", *Acta Chem. Scand.,* 24 pp. 2084–2100 (1970).

*Primary Examiner*—David M. Naff
*Attorney, Agent, or Firm*—Fitzpatrick, Cella, Harper & Scinto

[57] ABSTRACT

A biocatalyst such as an enzyme or microbe is immobilized in a polymer gel having a phase transition temperature such that it is capable of reversibly swelling and shrinking by a change in temperature. By lowering the temperature, the polymer gel is caused to swell and a biocatalyst is absorbed therein and by raising the temperature, the polymer gel is caused to shrink and immobilize the biocatalyst. The biocatalyst may then be released by cooling the polymer to cause it to swell. Only a portion of the polymer gel may be subjected to temperature change to immobilize the biocatalyst only in a desired portion.

22 Claims, 1 Drawing Sheet

BIOCATALYST IMMOBILIZATION WITH A REVERSIBLY SWELLING AND SHRINKING POLYMER

This application is a continuation of application Ser. No. 309,033 filed Feb. 2, 1989, now abandoned, which in turn is a continuation of application Ser. No. 880,320 filed June 30, 1986, now abandoned.

BACKGROUND OF THE INVENTION

1. Field of the Invention

This invention relates to a biocatalyst-immobilizing carrier (hereinafter referred to as an immobilizing carrier) wherein at least one biocatalyst such as an enzyme, a microbe or the like is stably immobilized in a carrier gel with the high activity of the catalyst being retained. More particularly, the present invention relates to a novel immobilizing carrier which can be utilized in such applications as (1) bioreactors for production of chemical substances, (2) biosensors for detection of chemical substances and (3) formation of color pattern or image utilizing a reaction by an organism such as an enzyme, a microbe or the like, as well as to a method for preparing an immobilized carrier.

2. Related Background Art

Techniques for biocatalyst immobilization are prerequisite as a basic technique for the development of biosensors or bioreactors, and researches on these techniques are actively under way throughout the world.

Reactions by a biocatalyst such as an enzyme, a microbe or the like, as compared with chemical reactions used in conventional chemical industrial processes, have the following advantages.

(1) Reactions proceed at a normal temperature and a normal pressure, giving energy-saving processes.

(2) A particular reaction (reaction specificity) takes place at the particular site (site specificity) of a compound of particular structure (substrate specificity) stereospecifically (stereospecificity). Therefore, no by-product is formed and a desired product can be obtained at a high yield and with a high purity.

(3) Since the substrate specificity of reaction is very high, only a desired compound can selectively be reacted even when various other compounds coexist. However, biocatalysts have the following drawbacks when used as they are. Since biocatalysts are generally water-soluble or otherwise used as an aqueous dispersion or in the presence of water, it is difficult to separate reaction products from raw materials, unreacted materials or biocatalysts used. Further, the catalytic activity of biocatalysts is lost by heat, organic solvents, acids and alkalies or even by reaction products. Thus, biocatalysts have been unable to fully exhibit their catalytic abilities.

Hence, research on biocatalyst immobilization by carrier has been conducted from around 1953. At present, the following four major methods are known for biocatalyst immobilization. (a) A bonding-to-carrier method wherein a biocatalyst is directly immobilized onto a insoluble carrier by covalent-bonding, physical adsorption, ionic-bonding or the like. (b) A crosslinking method wherein biocatalyst molecules are bonded with each other by a polyfunctional reagent and made insoluble. (c) An enclosing method wherein a biocatalyst is enclosed in a lattice-shaped polymer gel, microcapsules, a liquid lipid membrane (liposome) or the like. (d) A combination method wherein at least two of the above method (a), (b) and (c) are combined appropriately.

Of these, an enclosing method using a polymer gel is thought to have the widest application because the method enables the immobilization of not only a single biocatalyst but also a plurality of biocatalysts. These conventional immobilization methods, however, have various drawbacks such as the following. The original activity of biocatalyst is reduced by immobilization; biocatalysts are not immobilized stably and a part of them dissolves out of a carrier; the reactivation of immobilized biocatalyst after use is difficult or impossible; the procedure for immobilization is complicated; and the precise immobilization of biocatalyst onto the desired sites of carrier is difficult.

SUMMARY OF THE INVENTION

The present invention has been attained to remove the above drawbacks of the conventional immobilization techniques.

One object of the present invention is to provide a biocatalyst-immobilized carrier wherein a biocatalyst is precisely immobilized by a carrier at the desired portions of the carrier or in a desired pattern and wherein the immobilized biocatalyst is not detached easily and retains the original catalytic activity.

Another object of the present invention is to provide a method for immobilizing a biocatalyst wherein a biocatalyst is immobilized by a carrier at the desired portions of the carrier or in a desired pattern.

Still another object of the present invention is to provide a biocatalyst-immobilizing carrier wherein the biocatalyst after use can easily be reactivated, as well as to a method for preparing said carrier.

According to an aspect of the present invention, there is provided a biocatalyst-immobilizing carrier, which comprises a polymer gel capable of reversibly swelling and shrinking by action of heat for immobilizing at least one biocatalyst therein.

According to another aspect of the present invention, there is provide a method for immobilizing a biocatalyst, which comprises bringing a polymer gel capable of reversibly swelling or shrinking by the action of heat in a swelled state into contact with a liquid medium containing a biocatalyst, heating the polymer gel to its phase transition temperature or higher to convert the polymer gel to a shrinked state and thereby allowing the polymer gel to immobilize the biocatalyst.

According to a further aspect of the present invention, there is provided a method for immobilizing a biocatalyst, which comprises heating a desired portion of a polymer gel capable of reversibly swelling or shrinking by the action of heat to the phase transition temperature or higher of the gel to convert said portion to a shrinked state, bringing the polymer gel into contact with a liquid medium containing a biocatalyst, and thereby allowing the non-heated portion of the polymer gel other than the heated portion to immobilize the biocatalyst.

According to a still further object of the present invention, there is provided a method for immobilizing a biocatalyst, which comprises bringing a polymer gel capable of reversibly swelling or shrinking by the action of heat into contact, in its swelled state, with a liquid medium containing a biocatalyst, heating the polymer gel to phase transition temperature or higher of the gel to convert the polymer gel to a shrinked state and to allow the polymer gel to immobilize the biocatalyst and then cooling the desired portion of the polymer gel to a temperature lower than the phase transition temperature to release the biocatalyst out of the portion.

BRIEF DESCRIPTION OF THE DRAWINGS

FIG. 2A shows a polymer gel in a swelled state and FIG. 2B shows a polymer gel in a shrinked state.

DETAILED DESCRIPTION OF THE INVENTION

The function and constitution of the immobilizing carrier of the present invention will be described in detail by referring to the accompanying drawings.

Figure 2A:
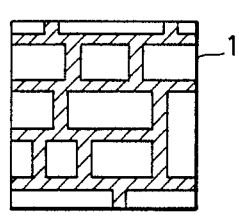
FIGS. 2A and 2B are schematic drawings showing a polymer gel carrier used in the present invention.
Figure 2B:
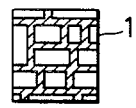

FIGS. 2A and 2B are schematic drawings showing a polymer gel substrate constituting the immobilizing carrier of the present invention. FIG. 2A shows the gel in its swelled state at low temperatures. FIG. 2B shows the gel in its shrinked state at high temperatures. In these figures, the hatched portions represent the reticular structure of the gel. Such a thermally shrinking or swelling property (a phase transition property) of the polymer gel substrate depends on the reticular structure of the polymer gel, tho structure of the polymer molecules constituting the gel, the salt concentration in a solution surrounding the gel, the pH of the solution, etc. Once these conditions are fixed, this phase transition takes place critically at one particular temperature corresponding to the fixed conditions and yet reversibly.

By selecting the above conditions, the phase transition temperature can be set within the range of, for example, 0° C. and 100° C. The reversible phase transition is very rapid (1 second or less) if the heat transfer is conducted sufficiently fast When the polymer gel shrinks by the action of heat, its porous reticular structure changes from a hydrophilic form to a hydrophobic form. As a result, permeation of a highly hydrophobic substance dissolved in a non-aqueous solvent, through the shrinked polymer gel, is facilitated and an effecitve and selective reaction between the hydrophobic substance in the non-aqueous solvent and the polymer gel is made possible.

Figure 1:
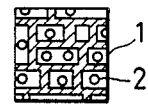
FIG. 1 is a schematic drawing showing a biocatalyst-immobilizing carrier of the present invention.
Figure 3A:
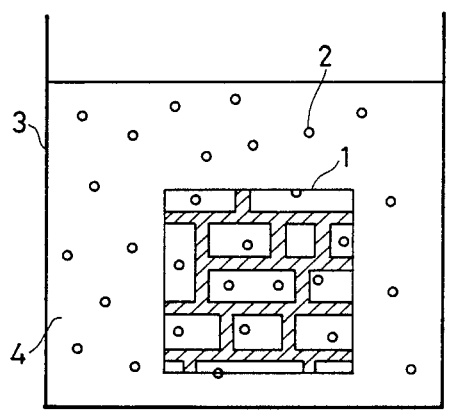
FIGS. 3A and 3B are schematic drawings showing a method for immobilizing a biocatalyst in a polymer gel carrier.
Figure 3B:
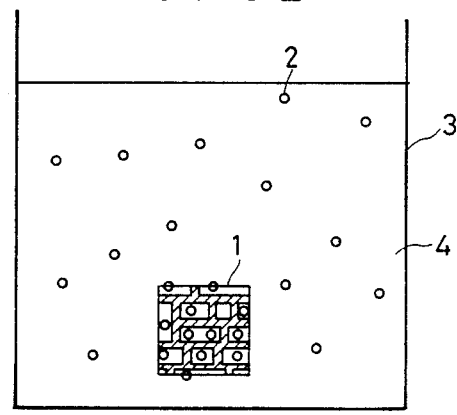

FIGS. 3A and 3B illustrate a method for immobilizing a biocatalyst in a carrier, used in the production of the immobilizing carrier of the present invention. At first, a gel in shrinked state as shown in FIG. 2B is immersed in a container 3 in FIG. 3A containing a solution 4 of a biocatalyst 2 such as an enzyme, fungus cells, a yeast or the like. Accordingly the gel temperature falls and the gel turns to a swelled state as shown in FIG. 2A, whereby the solution 4 containing the biocatalyst 2 is absorbed into the network of the gel 1. This state is represented by FIG. 3A. When the whole system is heated to the phase transition temperature or higher of the gel, the gel 1 of FIG. 3A shrinks and turns to a state illustrated in FIG. 3B. Consequently the majority of the solvent in the solution 4 is released out of the polymer gel but the biocatalyst 2 is retained in the network of the polymer gel and immobilized therein in a sufficiently large amount FIG. 1 shows an immobilized biocatalyst thus prepared. This immobilized biocatalyst in a shrinked state can be used as a biosensor or a bioreactor at temperatures where the immobilizing gel remains in its shrinked state.

The immobilizing carrier of the present invention is prepared by utilizing the fact that a polymer gel undergoes a rapid reversible phase transition by the action of heat Below the phase transition temperature, the gel interacts significantly with a solvent surrounding the gel such as water, and absorbs a large amount of the solvent into the gel network and accordingly is in a swelled state. Above the phase transition temperature of the gel, the molecular chains, particularly the side chains of the gel polymer reduce the affinity toward the solvent, whereby the solvent in the gel network is released out and the polymer gels agglomerate to become white turbid. Therefore, if a polymer gel of a relatively coarse network is selected, the gel can incorporate large molecules thereinto in its swelled state; and when the gel is made to transform to a shrinked state, the gel network also shrink and the large molecules incorporated into the gel are immobilized therein.

Since the immobilizing carrier of the present invention is used at temperatures at which the polymer gel constituting said immobilizing carrier is in a shrinked state, the phase transition temperature of the polymer gel is required to be at least lower than the deactivation temperature of the biocatalyst (e.g. an enzyme) immobilized by the polymer gel. Biocatalysts such as enzymes and the like show, in general high activities at about 0° to about 80° C.; therefore, it is desirable that the polymer gel have a phase transition temperature of 80° C. or below, preferably 70° C. or below. It is also desirable that the polymer gel have in general, a phase transition temperature of 0° C. or below, because the biocatalyst before being immobilized by the polymer gel is dissolved or suspended in a solvent composed substantially of water. Incidentaly, the phase transition temperature used above refers to a phase transition temperature of a polymer gel in water having a pH of about 7.

As mentioned above, in the immobilized carrier of the present invention, a biocatalyst is immobilized by a polymer gel at the desired portion of the gel or in a desired pattern, by utilizing the characteristic property of the gel that the gel undergoes a rapid and reversible phase transition by the action of heat. The immobilized carrier of the present invention can be prepared by the following methods, for example (A) At first, a polymer gel is heated in whole above its phase transition temperature to shrink (FIG. 2B). This polymer gel in shrinked state is allowed to tightly adhere to a heater capable of generating heat at the desired pattern portion and that portion of the heater is allowed to generate heat Subsequently the heater and the polymer gel adhering to the heater are immersed in a solution containing a biocatalyst, for a desired length of time. Thus the non-heated portions of the polymer gel other than the heated portion corresponding to the pattern portion of the heated portion corresponding to the pattern portion of the heater are cooled, and when the temperature of the non-heated portions of the polymer gel have fallen below the phase transition temperature of the polymer gel, the non-heated portion of the polymer gel swells and absorbs thereinto the solution containing a biocatalyst (FIG. 3A). When the non-heated portion of the polymer gel has sufficiently absorbed the biocatalyst, the whole polymer gel is heated above the phase transition temperature but below the temperature at which the biocatalyst causes no deactivation, whereby the biocatalyst absorbed into said portion is immobilized therein. In this method, the biocatalyst is immobilized in a particular pattern at the portions of the polymer gel not heated in the solution containing the biocatalyst. (B) A polymer gel is heated in whole above the phase transition temperature to be shrinked. Then, the polymer gel in shrinked state is immersed in a solution containing a biocatalyst. The temperature of the whole polymer gel is lowered and when the temperature has dropped lower than the phase transition temperature, the polymer gel swells and absorbs the biocatalyst therein (FIG. 3A). When the polymer gel has sufficiently absorbed the biocatalyst, the whole polymer gel is heated to a temperature which is higher than the phase transition temperature but at which the biocatalyst is not deactivated, so as to shrink the polymer gel and thereby to immobilize the biocatalyst in the whole polymer gel (FIG. 3B). Then this polymer gel is allowed to adhere to a heater which is generating a heat only at a desired pattern portion, and in this state, the polymer gel and the heater are immersed in, for example, water. The non-heated portion of the polymer gel other than the heated portion corresponding to the pattern portion of the heater are cooled and, when the temperature of said non-heated portion has dropped lower than the phase transition temperature, the non-heated portion of the gel swells and the biocatalyst immobilized in such a portion is released into water. Meanwhile, the portion of the polymer gel being heated by the heater is maintained in a shrinked state and therefore the biocatalyst immobilized will remain there in the desired pattern. When the biocatalyst has sufficiently been released out of the non-heated portions of the polymer gel, the whole polymer gel is taken out of water. In this method, the biocatalyst is immobilized in a desired pattern at the portion of the polymer gel heated in water by the heater.

When two or more different biocatalysts are immobilized by a single polymer gel, each at the desired portions of the gel or in a desired pattern, either of the above methods or their combination can be repeated for each biocatalyst.

As the polymer gel usable for the immobilizing carrier of the present invention, there can be mentioned three-dimensional reticular polymers which are obtained by (1) adding to a polymer composed substantially of a homopolymer or copolymer of polymerizable vinyl monomers (e.g. N-substituted acrylamide), a crosslinkable compound such as a compound having, in the molecule, a plurality of sites capable of causing a polymerization reaction (e.g. divinylbenzene or ethylene dimethacrylate) or a compound having, in the molecule, a site capable of causing a polymerization reaction and a site capable of causing a condensation or addition reaction (e.g. glycidyl methacrylate or N-methylolacrylamide) and then (2) reacting the polymer and the crosslinkable compound As the polymer gel, there may also be mentioned other three-dimensional reticular polymers which are obtained by subjecting a linear polymer such as a polyimine (e.g. a polyethyleneimine). a polyester (e.g. a polyoxyethylene adipoyl) or a polyamide (e.g. a polyglycine) to a polymer reaction using a crosslinking agent or a radiation to form a crosslinked structure. As the crosslinking agent used for the polymer reaction of polymers such as a polyethylene oxide, a polyethyleneimine and a polyglycine, there can be mentioned compounds having, in the molecule, a plurality of sites capable of causing a condensation or addition reaction, such as glutaraldehyde, dimethylolurea, epichlorohydrin and phenyl diisocyanate.

Particularly preferable are acrylamide type polymers prepared from at least one monomer selected from N-ethylacrylamide, N-n-propylacrylamide, N-n-propylmethacrylamide, N-isopropylacrylamide, N-isopropylmethacrylamide, N-cyclopropylacrylamide, N-cyclopropylmethacrylamide, N,N-ethylmethylacrylamide, N,N-diethylacrylamide, N-acrylpyrrolidine, N-acrylpiperidine, N-methylolacrylamide, etc.

Preferable as the crosslinking agent are N,N-methylene-bis(acrylamide), ethylene glycol dimethacrylate, etc.

As the liquid constituting the polymer gel, there can be mentioned an organic solvent such as water, an alcohol (e.g. methanol, ethanol), a ketone (e.g. acetone, methyl ethyl ketone), a hydrocarbon solvent (e.g. pentane, cyclohexane, benzene), a halogenated hydrocarbon solvent (e.g. tetrachloroethane, dichlorobenzene), an ester (e.g. isoamyl acetate, ethyl formate), an ether (e.g. dioxane, diglyme), an amide (e.g. dimethylformaide, dimethylacetamide), a sulfur-containing solvent (e.g. dimethylsulfoxide) or the like; a mixed solvent thereof; and a solution of a salt (e.g. lithium perchlorate, ammonium propionate), an organic compound (e.g. urea, glucose) or the like in said organic solvent or mixed solvent All of the polymer gels mentioned above have a characteristic property of reversibly swelling or shrinking by the action of heat. However, as set forth previously, their phase transition temperatures depend not only on the substrate polymer constituting each polymer gel but also on the salt concentration in the solution surrounding the polymer gel, the pH of the solution, etc. In order to obtain a polymer gel having a phase transition temperature which falls in a preferable range as mentioned previously, the raw materials (e.g. a linear polymer and a crosslinking agent) need be selected carefully because when, for example, an N-substituted acrylamide is used as a monomer for a linear polymer, use of an acrylamide having a hydrophobic N-substituent tends to give a low phase transition temperature of the polymer gel obtained and, in contrast, use of an acrylamide having a hydrophilic N-substituent tends to give a high phase transition temperature and also because a higher crosslink density will result in a higher phase transition temperature of the gel.

The polymer gel used for the immobilizing carrier of the present invention is also required to be able to easily absorb a biocatalyst such as an enzyme or the like in the swelled state of the gel. In other words, the polymer gel must allow the free passage of a biocatalyst through the gel in the swelled state of the gel. In this connection, the polymer gel as a carrier of the present invention must have a fairly coarse network, as compared with conventional carrier gels for immobilization. Such a coarse network of the polymer gel may preferably be obtained by employing a crosslinking agent in an amount 0.1 to 10% by weight based on the monomer for the linear polymer in preparing the polymer gel by crosslinking method.

The polymer gel as a carrier for biocatalyst immobilization may be in any shape. The shape may be a bead, a block, a sheet, a film, a cloth, a bundle of thin fibers, a laminated film, etc.

The biocatalyst used in the present invention is, in most cases, an enzyme or a microbe such as a bacterium, a mold fungi, an yeast, a ray fungi, an alga, a protozoa or the like As the enzyme, there can be mentioned, for example, the followings.

(1) Oxidoreductases Alcohol dehydrogenase, glucose oxidase (2) Hydrolases Acetylcholinesterase, trypsin, chymotrypsin, thrombin, urease, aminoacylase, lipase (3) Transferases Amino-acid transacetylase lactose synthetase (4) Lyase Tyrosine decarboxylase (5) Isomerases Retinal isomerase, glucose isomerase As the coenzyma, there are mentioned NAD, FMN, PMP, PLP, CoA, etc.

Examples of the microbe include molds belonging to Penicillium genus; etc.; bacteria belonging to Brevibacterium genus, Escherichia genus (e.g. Escherichia coli), etc.; yeasts belonging to Candida genus, Debaryomyces genus, etc.; and a ray fungi belonging to Streptomyces genus.

These biocatalysts can be immobilized alone or in combination of two more and also in the presence of an inorganic salt.

When the biocatalyst-immobilizing carrier is employed as a sensor or a reactor, the life of the biocatalyst immobilized is important. In most cases, the biocatalyst, once used, need be reactivated.

The reactivation of the biocatalyst-immobilizing carrier of the present invention can easily be conducted according to the following procedure. An immobilizing carrier whose catalytic activity has deteriorated is washed in a condition where the carrier gel causes swelling, to release a biocatalyst (e.g. an enzyme) of reduced activity out of the gel. The gel is then immersed in an aqueous solution containing a fresh biocatalyst and is allowed to undergo a phase transition from a shrinked state to a swelled state, whereby the fresh biocatalyst is introduced into the gel. Thereafter, the gel in swelled state is allowed to shrink to immobilize the fresh biocatalyst in the gel. Thus is conducted the reactivation of the immobilizing carrier. By repeating this procedure as necessary, the reactivation of the immobilized carrier a number of times is possible. This reactivation can be conducted with the immobilized carrier as integrated in a sensor or a reactor and accordingly is easy and has wide applications.

When the above reactivation procedure for the immobilized carrier is applied only to the desired portion(s) of the polymer gel, the reactivation of the very portion(s) of the polymer gel becomes possible.

The immobilized carrier of the present invention has many advantages such as the followings.

(1) A biocatalyst can be immobilized in high efficiency with less elimination and less deactivation.

(2) Immobilization procedure is simple.

(3) The biocatalyst immobilizing carrier after use can easily be reactivated.

(4) At least one biocatalyst can be immobilized by a carrier polymer gel at the desired portion(s) of the gel or in a desired pattern. This has made it possible to provide an immobilizing carrier for use in biosensors and bioreactors immobilizing at least one biocatalyst at the desired portion(s) or in a desired pattern, or in color patterns and images of at least one color utilizing a biocatalyst reaction.

(5) It has become possible to provide an immobilizing carrier capable of effectively reacting with a highly hydrophobic substrate dissolved in a non-aqueous solvent.

The present invention will be described in more detail below by way of Examples.

EXAMPLE 1

Preparation of biocatalyst-immobilizing carrier 5 g of isopropylacrylamide, 80 mg of N,N-methylenebis-(acrylamide) and 30 mg of ammonium persulfate were dissolved in 100 ml of cold water. Thereto was added 60 μl of tetramethyl-ethylenediamine and the solution was degassed by an aspirator. Immediately, the solution was introduced into a gap of 10 μm formed by two glass plates with a Mylar film interposed therebetween as a spacer, and polymerization was conducted at room temperature. After the completion of the polymerization, the glass plates were peeled off and the polymerization product was washed with water to obtain a film-shaped gel of 30 mm×30 mm×about 10 μm (thickness). This gel film shrinked and became cloudy at about 30° C. or above and, when cooled, rapidly swelled and became transparent.

The gel film was heated to about 35° C. to shrink and, in that state, was immersed in 10 ml of an aqueous solution of 25° C. containing 1% of glucose oxidase, an oxidoreductase. Immediately, the gel film began to swell and absorbed the enzyme thereinto. In about 5 minutes, the whole system was heated to about 35° C., and the gel shrinked and became white turbid. This gel film in shrinked s&ate was taken out and washed with hot water of 35° C. to obtain a desired thin gel film having immobilized glucose oxidase therein.

The ratio of enzyme immobilized in gel was 90% or more calculated from the enzyme amounts in the remaining solution and the washings. The activity of enzyme right after immobilization, measured according to the ordinary method was 90% or above of the activity before immobilization. Further, the enzyme-immobilized gel film was immersed in hot water of 35° C. for 100 days, and the activity of enzyme after 100 days as well as the amount of enzyme detached after 100 days were measured. The activity decreased by at least 5% as compared with the activity right after immobilization, and the amount of enzyme detached was 1% or below of the amount right after immobilization.

EXAMPLE 2

A film-shaped gel of 30 mm×30 mm×about 10 μm (thickness) was prepared in the same manner as in Example 1 except that isopropylacrylamide used in Example 1 was replaced by N-acrylpiperidine. This gel film shrinked and became white turbid at a temperature of about 5° C. or higher and swelled and became transparent at a temperature of 5° C. or lower. Therefore, it shrinked and was white turbid at room temperature (20° C.).

The gel film was immersed in 10 ml of an aqueous solution of 2° C. containing 1% of chymotrypsin, a hydrolase. Immediately, the gel film swelled and absorbs the enzyme solution therein. About 5 minutes later, the whole system was heated to about 20° C. The gel shrinked and became white turbid The gel film in shrinked and white turbid state was taken out and washed with pure water of 20° C. to obtain a desired thin gel film having immobilized chymotrypsin therein.

The immobilization ratio of the enzyme in the gel film, measured in the same method as in Example 1 was 98% or above. The activity of enzyme right after immobilization, measured according to the conventional method was 100 % of the activity before immobilization. Further, the enzyme-immobilized gel film was immersed in hot water of 35° C. for 100 days, and the activity of enzyme after 100 days as well as the amount of enzyme detached after 100 days were measured. The activity decreased by 1% or less as compared with the activity right after immobilization, and the amount of enzyme detached was 0.1% or less of the amount right after immobilization.

EXAMPLE 3

Reactivation of biocatalyst-immobilizing carrier

The gel film incorporating immobilized chymotrypsi as prepared in example 2 was immersed in hot water of about 60° C. to reduce the original activity by at least 50%. The gel film was immersed in pure water of 2° C. and was allowed to stand in running water for 10 minutes. Then, the gel film was immersed in warm water of about 25° C. to shrink. Subsequently the gel film was immersed in 10 ml of an aqueous solution of 2° C. containing 11% of chymotrypsin. Immediately, the gel film swelled and absorbed the enzyme solution therein. About 5 minutes later, the whole system was heated to about 20° C., whereby the gel shrinked and became white turbid. The shrinked and turbid gel film was taken out and washed with pure water of 20° C. to obtain a desired gel film having immobilized chymotrypsin therein and having recovered original activity.

That is, the activity and immobilization ratio of this gel film were measured and found to be the same values, respectively, as those obtained in Example 2, which shows that the enzyme-immobilizing gel film was reactivated.

EXAMPLE 4

The gel film incorporating immobilized chymotrypsin as prepared in Example 2 was immersed in 20 ml of a 3% solution (pH=8) of indoxyl acetate dissolved in water/ acetonitrile (1/9 by volume). The white turbid gel surface gradually turned blue and, one minute later, the whole gel film had a deep blue color in the solution. This proves that the immobilized enzyme is stable and keeps the activity even in an organic solvent. For comparison, chymotrypsin itself was added to the same indoxyl acetate solution, but no color development reaction took place.

EXAMPLE 5

Preparation of biocatalyst-immobilizing carrier 5 g of isopropylacrylamide, 80 mg of N,N-methylene-bis-(acrylamide) and 30 mg of ammonium persulfate were dissolved in 100 ml of cold water. Thereto was added 60 μl of tetramethyl-ethylenediamine, and the solution was degassed by an aspirator. Immediately, the solution was poured into a gap of 2 mm formed by two glass plates with a Mylar film interposed between the plates as a spacer, and polymerization was conducted at room temperrture. After the completion of the polymerization, the glass plates were peeled off and the polymerization product was washed with water to obtain a film-shaped gel of 30 mm×30 mm×about 2 mm (thickness). This gel film shrinked and became white turbid at about 30° C. or above and, when cooled, rapidly swelled and became transparent The gel film was heated to about 35° C. to shrink and, in that state, was immersed in 10 ml of an aqueous solution of 25° C. containing 1% of glucose oxidase, an oxidoreductase. Immediately, the gel film began to swell and absorbed the enzyme thereinto. In about 5 minutes, the whole system was heated to about 35° C., and the gel shrinked and became white turbid. The gel film in shrinked state was taken out and washed with warm water of 35° C. to obtain a desired thin gel film having immobilized glucose oxidase therein The ratio of enzyme immobilized in gel was calculated from the enzyme amounts in the remaining solution and the washings, both measured according to the enzymatic activity test method. It was 90% or above. The activity of enzyme right after immobilization, measured according to the conventional method was 90% or above of the activity before immobilization. Further, the enzyme immobilized gel film was immersed in hot water of 35° C. for 100 days, and the activity of enzyme after 100 days as well as the amount of enzyme detached after 100 days were measured. The activity decreased by at least 5% as compared with the activity right after immobilization, and the amount of enzyme detached was 1% or below of the amount right after immobilization.

The enzyme-immobilized gel film obtained above was allowed to tightly adhere to a heater which was generating heat in a pattern of stripes. The gel film and the heater in this state were immersed in pure water of 20° C. and allowed to stand in a flow of pure water for about 1 hour with the film portions on the hot (35° C.) stripe portions of the heater being maintained in a white turbid and shrinked state and with the non-heated other film portions being maintained in a transparent state. Subsequently the gel film was taken out of water and measured for its enzymatic activity and enzyme immobilization ratio. With respect to the enzyme immobilization ratio, the ratio of (a) the total enzyme amount immobilized in the original gel film film before enzyme release to (b) the enzyme amount remaining in the gel film after enzyme release, calculated from (a) and the enzyme amount present in the water which had been contacted with the gel film was identical to the ratio of the total gel film area to the area of the gel film portions corresponding to the stripe portions of the heater. With respect to the enzymatic activity, the gel film portions corresponding to the stripe portions of the heater had an enzymatic activity of 90% or above of that of the enzyme before immobilization.

EXAMPLE 6

The gel film wherein glucose oxidase had been immobilized in a stripe pattern, obtained in Example 5 was heated in whole to about 35° C. to shrink it. The gel film in shrinked state was allowed to adhere to a heater capable of generating heat in a stripes pattern and the glucose oxidase-immobilized portions of the gel film were heated to aout 35° C. by the heater. In this state, the gel film and the heater were immersed in 10 ml of a 1% aqueous chymotrypsin solution of 25° C. The glucose oxidase-immobilized portions of the gel film on the heat generating portions of the heater were kept in a white turbid and shrinked state and the nonheated portions of the gel film immediately started to swell and absorbed the enzymatic solution thereinto. About 5 minutes later, the whole system was heated to about 35° C., whereby the non-heated portions of the gel film also shrinked and became white turbid. Lastly, the gel film was taken out and washed with warm water of 35° C. to obtain an immobilized gel film wherein the glucose oxidase-immobilized portions and the chymotrypsinimmobilized portions were arranged alternately in stripes.

EXAMPLE 7

The gel film incorporating the immobilized enzyme as prepared in example 6 was immersed in 30 ml of a solution (35° C.) of 3% of indoxyl acetate, 2% of glucose and 2% of Leuco Auramine in water/acetonitrile (1/1 by volume). The cloudy gel surface gradually turned to a colored surface consisting of alternating blue and yellow stripes. There was thus formed a stripe pattern consisting of two alternate colors.

EXAMPLE 8

Reactivation of enzyme-immobilizing carrier

The gel film wherein glucose oxidase had been immobilized in a stripe pattern, prepared in example 5 was immersed in hot water of about 80° C. for 30 minutes.

After the immersion, the gel film was measured for its enzymatic activity according to the ordinary method. The film was deactivated by at least 50% of the original activity.

This activity-reduced gel film was immersed in pure water of 25° C. and allowed to stand in running water for 10 minutes. Then, the film was immersed in hot water of about 35° C. to shrink it and subsequently was immersed in 10 ml of a 1% aqueous glucose oxidase solution of 25° C. Immediately, the gel film swelled and absorbed the enzyme solution thereinto. About 5 minutes later, the whole system was heated to about 35° C. and the gel shrinked and became white turbid. The shrinked and turbid gel film was taken out and washed with pure water of 35° C. to obtain a gel film having immobilized glucose oxidase all over.

This gel film was treated in the same manner as in Example 5 to obtain a gel film having immobilized glucose oxidase in a stripes pattern.

This gel film was measured for the enzymatic activity and the amount of enzyme immobilized. The same values as in Example 5 were obtained and the successful reactivation of the activity-reduced immobilized gel film was confirmed.

We claim:

1. A method for immobilizing a biocatalyst, which comprises:
   (a) reducing the temperature of a three dimensional reticular polymer gel, said polymer gel having a specific phase transition temperature at which said polymer gel reversibly swells and shrinks, below said specific phase transition temperature to cause said polymer gel to swell;
   (b) thereafter contacting said polymer gel in said swollen state with a liquid medium containing a biocatalyst to allow said biocatalyst to absorb into said polymer gel; and
   (c) thereafter heating at least a portion of said polymer gel to said phase transition temperature or higher thereby shrinking said portion of said polymer gel to immobilize said absorbed biocatalyst at said portion.

2. A method according to claim 1, wherein the phase transition temperature of the polymer gel in water is lower than the deactivation temperature of the biocatalyst.

3. A method according to claim 1, wherein the biocatalyst is an enzyme or a microbe.

4. A method according to claim 1, wherein said biocatalyst is immobilized at a predetermined pattern of the polymer gel.

5. A method according to claim 1, wherein the polymer gel has a phase transition temperature between 0° C. and 80° C.

6. A method according to claim 1, wherein the liquid medium is composed mainly of water.

7. A method for immobilizing a biocatalyst, which comprises:
   (a) heating at least a portion of a three-dimensional reticular polymer gel to convert said portion to a shrunken state; said polymer gel having a phase transition temperature at which said polymer gel reversibly swells and shrinks;
   (b) contacting said polymer gel with a liquid medium containing a biocatalyst
   (c) allowing said biocatalyst to absorb into a non-heated portion of said polymer gel; and
   (d) heating said non-heated portion of said polymer gel to said phase transition temperature or higher thereby shrinking said non-heated portion to immobilize the biocatalyst at said non-heated portion.

8. A method according to claim 7, wherein during the contacting step the polymer gel is immersed in the liquid medium.

9. A method according to claim 7, wherein the phase transition temperature of the polymer gel in water is lower than the deactivation temperature of the biocatalyst.

10. A method according to claim 7, wherein the biocatalyst is an enzyme or a microbe.

11. A method according to claim 7, wherein said biocatalyst is immobilized at a predetermined portion of said polymer gel.

12. A method according to claim 7, wherein the polymer gel has a phase transition temperature between 0° C. and 80° C.

13. A method according to claim 7, wherein the liquid medium is composed mainly of water.

14. The method according to claim 7, wherein the biocatalyst is immobilized by the polymer gel in a desired pattern.

15. A method for immobilizing and releasing a biocatalyst, which comprises:
   (a) contacting a three-dimensional reticular polymer gel in a swelled state with a liquid medium containing a biocatalyst; said polymer gel having a phase transition temperature at which said polymer gel reversibly swells and shrinks;
   (b) allowing said biocatalyst to absorb into said polymer gel;
   (c) heating at least a portion of said polymer gel to said phase transition temperature or higher thereby shrinking said portion of said polymer gel to immobilize the biocatalyst at said portion; and
   (d) cooling said portion of the polymer gel to a temperature lower than the phase transition temperature to release the biocatalyst from said portion.

16. A method according to claim 15, wherein during the contacting step the polymer gel is immersed in the liquid medium.

17. A method according to claim 15, wherein the phase transition temperature of the polymer gel in water is lower than the deactivation temperature of the biocatalyst.

18. A method according to claim 15, wherein the biocatalyst is an enzyme or a microbe.

19. A method according to claim 15, wherein said biocatalyst is immobilized at a predetermined portion of said polymer gel.

20. A method according to claim 15, wherein the polymer gel has a phase transition temperature between 0° C. and 80° C.

21. A method according to claim 15, wherein the liquid medium is composed mainly of water.

22. The method according to claim 15, wherein the biocatalyst is immobilized by the polymer gel in a desired pattern.

* * * * *

UNITED STATES PATENT AND TRADEMARK OFFICE
CERTIFICATE OF CORRECTION

PATENT NO. : 4,975,375

DATED : December 4, 1990

INVENTOR(S) : MASAHIRO HARUTA ET AL.

It is certified that error appears in the above-identified patent and that said Letters Patent is hereby corrected as shown below:

COLUMN 1

Line 62, "a" should read --an--.
    Line 65, "pclyfunctional" should read --polyfunctional--.

COLUMN 2

Line 41, "provide" should read --provided--.

COLUMN 3

Line 30, "tho" should read --the--.
    Line 40, "fast When" should read --fast. When--.
    Line 66, "amount FIG. 1" should read --amount. FIG. 1--.

COLUMN 4

Line 6, "heat Below" should read --heat. Below--.
    Line 19, "shrink" should read --shrinks--.
    Line 28, "general high" should read --general, high--.
    Line 32, "have in" should read --have, in--.
    Line 36, "Incidentaly," should read --Incidentally,--.
    Line 46, "example (A)" should read --example. ¶ (A)--.
    Line 51, "heat Subse-" should read --heat. Subse---.

COLUMN 5

Line 3, "biocatalyst. (B)" should read
          --biocatalyst. ¶ (B)--.

UNITED STATES PATENT AND TRADEMARK OFFICE
CERTIFICATE OF CORRECTION

PATENT NO. : 4,975,375

DATED : December 4, 1990

INVENTOR(S) : MASAHIRO HARUTA ET AL.

It is certified that error appears in the above-identified patent and that said Letters Patent is hereby corrected as shown below:

COLUMN 6

Line 68, "an yeast," should read --a yeast,--.

COLUMN 7

Line 1, "like As" should read --like. As--.
    Line 2, "followings." should read --following.--.
    Line 11, "coenzyma," should read --coenzyme,--.
    Line 51, "followings." should read --following.--.
    Line 55, "biocatalyst immobilizing" should read --biocatalyst-immobilizing--.

COLUMN 8

Line 28, "s&ate" should read --state--.
    Line 59, "sorbs" should read --sorbed--.
    Line 61, "turbid The" should read --turbid. The--.
    Line 68, "conventioned" should read --conventional--.

COLUMN 9

Line 13, "chymotrypsi" should read --chymotrypsin--.
    Line 14, "example 2" should read --Example 2--.

COLUMN 10

Line 14, "enzyme immobilized" should read --enzyme-immobilized--.
    Line 36, "film film" should read --film--.
    Line 55, "aout" should read --about--.

UNITED STATES PATENT AND TRADEMARK OFFICE
CERTIFICATE OF CORRECTION

PATENT NO. : 4,975,375
DATED : December 4, 1990
INVENTOR(S) : MASAHIRO HARUTA ET AL.

Page 3 of 3

It is certified that error appears in the above-identified patent and that said Letters Patent is hereby corrected as shown below:

COLUMN 11

Line 1, "chymotrypsinim-" should read --chymotrypsin-im---.
    Line 6, "example 6" should read --Example 6--.
    Line 18, "example 5" should read --Example 5--.
    Line 47, "three dimensional" should read --three-dimensional--.

COLUMN 12

Line 2, "pattern" should read --portion--.
    Line 17, "biocatalyst" should read --biocatalyst;--.

Signed and Sealed this

Twentieth Day of October, 1992

Attest:

DOUGLAS B. COMER

Attesting Officer      Acting Commissioner of Patents and Trademarks